United States Patent [19]

Sollich

[11] Patent Number: 4,889,434

[45] Date of Patent: Dec. 26, 1989

[54] APPARATUS FOR DETERMINING CRYSTALLIZATION SOLIDIFICATION CURVES OF CHOCOLATE MASSES AND SIMILAR FATTY MASSES

[75] Inventor: Helmut Sollich, Rabenkirchen, Fed. Rep. of Germany

[73] Assignee: Sollich GmbH & Co. KG, Fed. Rep. of Germany

[21] Appl. No.: 179,578

[22] Filed: Apr. 8, 1988

[30] Foreign Application Priority Data

May 6, 1987 [DE] Fed. Rep. of Germany ....... 3714951

[51] Int. Cl.$^4$ .............................................. G01N 25/00
[52] U.S. Cl. .................................... 374/25; 374/16; 374/102; 241/278 R
[58] Field of Search ................... 374/25, 26, 16, 102, 374/138, 147, 148, 158, 218; 426/231, 233, 631; 241/278 R

[56] References Cited

FOREIGN PATENT DOCUMENTS 2015894A 9/1979 United Kingdom ............ 241/278 R
114152 6/1986 Japan ................................ 374/25
449289 11/1974 U.S.S.R. ........................... 374/26
402789 10/1983 U.S.S.R. ........................... 374/25

Primary Examiner—William A. Cuchlinski, Jr.
Assistant Examiner—Jeffrey Hohenshell
Attorney, Agent, or Firm—Max Fogiel

[57] ABSTRACT

An apparatus for determining crystallization solidification curves of chocolate masses and similar fatty masses is equipped with a measuring chamber 8 which is formed by a cooled wall and into which projects a temperature-measuring sensor 16. Here, the liquid chocolate mass is brought to solidification. A device for recording the temperature pattern in the solidifying chocolate mass against time is provided. A piston/cylinder unit 6, 7 which is arranged so as to dip with its open end face 10 into the chocolate mass to be measured serves as a measuring chamber 8. A drive is provided for the stroke of the piston 7. The piston 7 carries the temperature-measuring sensor 16. A device 6 for removing the solidified sample from the piston 7 and temperature-measuring sensor 16 is also provided.

11 Claims, 3 Drawing Sheets

APPARATUS FOR DETERMINING CRYSTALLIZATION SOLIDIFICATION CURVES OF CHOCOLATE MASSES AND SIMILAR FATTY MASSES

BACKGROUND OF THE INVENTION

The invention relates to an apparatus for determining crystallization solidification curves of chocolate masses and similar fatty masses, with a measuring chamber which is formed by a cooled wall, into which projects a temperature-measuring sensor. In this measuring chamber, the liquid chocolate mass is brought to solidification, and a device records the temperature pattern in the solidifying chocolate mass in relation to time.

Before chocolate mass is processed from the liquid state and brought to solidification, it has to be heat-treated as is known; that is, it is first heated and thus brought into the liquid state and subsequently cooled, until the fatty fraction in the chocolate mass forms solidification crystals. This process is also known as pre-crystallization. The properties of the solidified chocolate mass differ according to the composition of the chocolate mass and the heat-treatment process used. For a good gloss, a long shelf life and fine-grained breaking of the final product, it is important that, during heat treatment, fat crystals are formed in a crystal form which is high-melting in temperature terms and that these crystal agglomerates have small dimensions and are distributed homogeneously in the chocolate mass. The degree of heat-treatment or of precrystallization, which is the fraction of solidified fat crystals, is also critical for the production flow. Too low a fraction (inadequate heat-treatment) undoubtedly causes excessively long solidification times during final cooling and can result in a poor gloss and low shelf life. Too high a solidification fraction (excessive heat-treatment) gives rise to an increased viscosity of the chocolate mass to be processed and can result in less contraction during final cooling, a poor gloss and, again, a lower shelf life.

A known apparatus of the type described in the introduction makes it possible to determine crystallization solidification curves. Sampling vessels are used, consisting essentially of a portion of copper tube, on which a small cylindrical container which represents a measuring chamber is formed in one end region. This measuring chamber is filled with liquid chocolate mass. A temperature-measuring sensor is introduced manually into the measuring chamber, that is, it is inserted into the liquid chocolate mass. The other end of the measuring sensor is connected to a recording instrument which, at intervals of time, records the particular temperature of the solidifying chocolate mass. To ensure cooling, the sampling vessel consisting of a copper tube is subjected to cooling at its lower end by being dipped into a vessel containing an ice-water mixture. As a result of the conduction of heat in the copper tube, the liquid chocolate mass in the measuring chamber is also brought to solidification, specifically in a way which can be reproduced over a period of time. A thermocouple can be used, for example, as a temperature-measuring sensor. In the device for recording the temperature pattern, a paper strip is constantly moved sideways, so that the solidification curves are recorded and thus captured. It is therefore possible, during a production operation, for the heat treatment of the chocolate mass to be processed to be checked repeatedly at intervals of time, in order to ascertain that the heat treatment is being maintained at the desired or necessary level. Correcting measures can then also be taken on the heat-treatment machine accordingly. On the one hand, the known apparatus involves a high outlay, because an attendant is needed to extract the liquid chocolate mass, introduce it into the measuring chamber and carry out the measurement. Furthermore, the measurement is also unreliable since as it is possible for the operation to take place on a completely erroneous basis. Thus, the reference temperature can even deviate from 0° without being noticed. The liquid chocolate mass can experience a change between extraction at the checking point and introduction into the measuring chamber. Due to the possibility of these events, it is difficult to maintain reproducible conditions here. Moreover, the liquid chocolate mass can be extracted only at an open location on a heat-treatment machine or another processing station, and not in a closed pipeline or at other points, where access is difficult. Finally, the sampling vessels have to be cleaned again after the chocolate mass has solidified. For all these reasons, the intervals of time at which such monitoring checks are carried out are often very long.

SUMMARY OF THE INVENTION

The object on which the invention is based is to develop an apparatus of the type described in the introduction in such a way that sampling and determination of the crystallization solidification curve can take place automatically with the least possible manual involvement, specifically even at locations where access is otherwise difficult such as enclosed pipelines.

According to the invention, this is achieved by the measuring chamber which is a piston/cylinder unit being arranged so as to dip with its open end face into the chocolate mass to be measured. There is a drive for the stroke of the piston. The piston carries the temperature-measuring sensor, and a device for removing the solidified sample from the piston and measuring sensor is provided. A measuring chamber which is fixed in place and which communicates by means of its open end face with the chocolate mass to be measured, is thus created. As a result of the controllable stroke of the piston, it is possible to both fill the measuring chamber with liquid chocolate mass by suction and to eject the solidified cylindrical shaped body of chocolate mass out of the measuring chamber again by pressure. Furthermore, a device for removing the solidified sample from the piston and measuring sensor must be provided, because the solidified cylindrical body of chocolate mass does not dissolve by itself after being ejected from the measuring chamber. Since the temperature differences in this region are relatively small, it also cannot be assumed that the solidified sample will be removed as a result of a melting process. Because the piston carries the temperature-measuring sensor, it is possible for the measuring sensor to always be placed at a representative and indeed identical point in the measuring chamber, so that reproducible measurement results can be obtained. This new apparatus no longer needs human involvement; that is it is possible to set up a control program for this apparatus, by means of which samples can be taken even at relatively short intervals of time. These samples can be checked, recorded or otherwise stored or picked up and processed further for the purpose of controlling the heat-treatment machine or other parts of the installation. Faults which arise in the apparatus as a result of human involvement are avoided. The apparatus can be used not only in closed systems and at locations where access is difficult, but also in those places where the chocolate mass is under pressure. If the new apparatus is arranged at a suitable point, it can also be used perfectly well for controlling precrystallization devices. As a result of the stroke by which the solidified chocolate slug is ejected from the measuring chamber, the sample returns to the circuit automatically. There is no need to clean the sampling vessels used previously, and after such an ejection operation the apparatus is immediately ready again to determine a further solidification curve. Of course, depending on the activation of the apparatus, it is also possible to initiate or trigger this manually in a controlled manner. In terms of control, the novel apparatus affords completely new possibilities resulting, finally in an increase in the quality of the final product. Examples are biscuit bar covered with a chocolate mass, the manufacture of individual chocolates and easier mould removal of bar chocolate or hollow shapes. Heat treatment can be carried out more accurately, and because of this, there are fewer rejects in the final product.

The piston is appropriately designed so that it can be introduced, with its end face limiting the measuring chamber, into the chocolate mass to be measured, up to a point beyond the open end face of the cylinder. Of course at the same time, the piston does not leave its guide in the cylinder. As a result of this design, it is possible for the device which removes the solidified sample to be fixed in place. There will still be sufficient gap, through which new liquid chocolate mass to be checked can flow or move into the measuring chamber during the suction stroke of the piston. It is also possible, of course, either solely or additionally, for the device for removing the solidified sample to be arranged movably. This means mobility in the direction of the piston stroke. In any event, it is important that the device for removing the solidified sample also covers the end face of the piston and the temperature-measuring sensor arranged there.

A mechanical comminuting device, especially a milling or cutting device, has proved especially advantageous as a device for removing the solidified sample. This mechanical comminuting device should be designed so that the cylindrical solidified chocolate slug is comminuted or milled and removed in very small pieces. Such small pieces can be melted as a result of the stream of liquid chocolate mass and its heat content, to the extent that they do not impede the production flow.

The mechanical comminuting device can be arranged opposite the measuring chamber and adjacent to the end face of the piston in the extended position. Thus, the essential part of this mechanical comminuting device (for example, a milling head), assumes the temperature of the liquid chocolate mass, thus causing neither excessive heat treatment nor inadequate heat treatment, and furthermore making it possible to clean the end face of the piston and the measuring sensor after each sample. It is also advantageous if the end face of the piston projects into the stream of liquid chocolate mass and thus assumes, at least approximately, the temperature of the liquid chocolate mass. During the return stroke, also called the suction stroke, the piston then moves into another local region, in particular that of the cooled wall of the cylinder. It assumes the temperature of the cooled cylinder wall, which is the essential limiting surface of the measuring chamber, thus providing reproducible conditions for the solidification of the chocolate mass.

The wall of the piston/cylinder unit can be doubled and connected to a cooling circuit of constant temperature. For example, a temperature of 15° C. is suitable. However, also suitable, only coordination or calibration of the provided there exists coordination or calibration of the corresponding temperature measurements, other temperatures are, of course, also suitable. There is a simple way to keep this ratio as constant as possible, so that reproducible working results can be obtained with the apparatus.

The drive for the piston is appropriately made reversible and of adjustable stroke. Consequently, not only the suction of the liquid chocolate mass but also the ejection of the solidified slug can take place automatically or by program control. The adjustability of the stroke is expedient in order to provide constant conditions for successive measurements.

There are various possibilities for driving the piston. For example, a spindle motor with a step-down gear can be provided. The piston, on its rear side, can have or be extended into a threaded spindle, with which, for example, an axially mounted worm wheel interacts in order to convert a rotation into an axial movement of the piston.

The temperature-measuring sensor is expediently arranged centrally on the piston so as to project beyond the end face of the piston and measure the temperature in the solidifying chocolate mass at a representative point, specifically always at the same point. Of course, the device for removing the solidified sample must be designed so that the shaping of the end face of the piston with the projecting measuring sensor is not damaged. For example, the milling tool can have a recess which leaves the measuring sensor free.

The cylinder is appropriately equipped with thermal insulation in the region of its open end face. Likewise, the piston can have thermal insulation in the region of its end face and of the mounting of the temperature-measuring sensor, so that the temperature conditions are more specific, and the comparatively hot liquid chocolate mass in the container or in the pipe to be measured is prevented from influencing the solidifying sample.

The apparatus is explained further and described in a preferred exemplary embodiment.

DESCRIPTION OF THE PREFERRED EMBODIMENT

The apparatus illustrated in the Figures is shown being used on a pipeline. A pipeline section 1 expediently equipped with flanges, in order to be connected to a pipeline or a container, has liquid chocolate mass 2 which is heat-treated and is to be checked flowing through it in the direction of the arrows 3,4. chocolate mass 2 which is heat-treated and is to be The pipeline section 1 is expediently designed as a double casing and has pockets 5 which are connected to a water circuit. When the apparatus is in operation, hot water, for example, at approximately 40° C., flows through these pockets 5, in order to melt the solidified mass in pipeline section 1. During continuous operation, the temperature of this circuit can be kept constant, at 32° C., for examples, depending on the particular application and use. The entire apparatus could also be attached to an open container or the like, at a location where the liquid heat-treated chocolate mass is finally to be checked.

Figure 1:
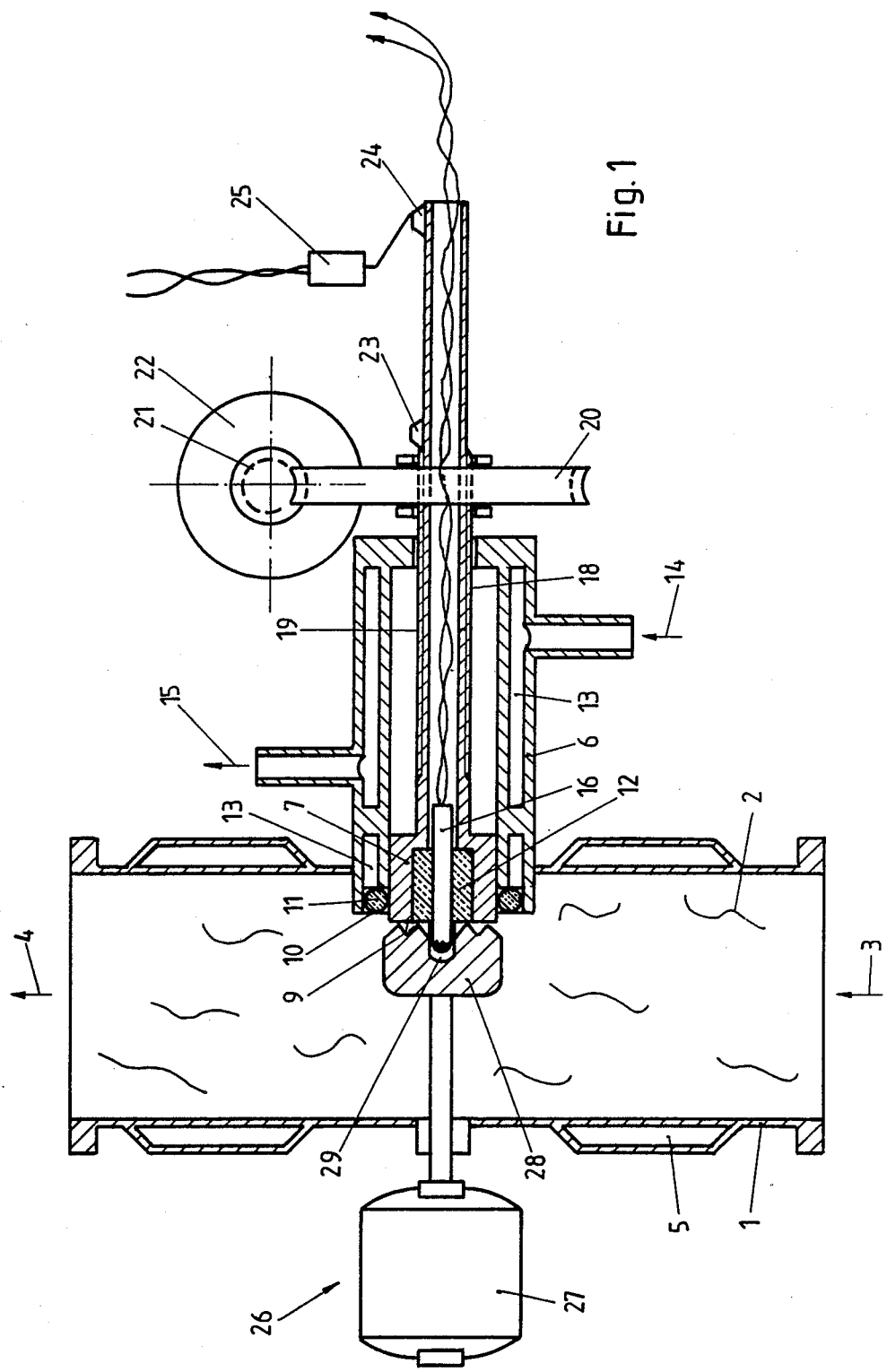
FIG. 1 shows the relative position of the essential parts of the apparatus in the state of rest.

The actual apparatus has essential components consisting of a cylindrical housing 6 and a piston 7, which together form a piston/cylinder unit 6, 7. The cylindrical housing 6 encloses a measuring chamber 8 (FIG. 2) which, during the suction stroke of the piston 7 receives the liquid chocolate mass to be checked. In FIG. 1, the piston 7 is in its front dead-center position and is advanced so as to project with its end face 9 beyond the end face 10 of the cylindrical housing 6. The cylindrical housing 6 is equipped with thermal insulation 11 in the region of the end face 10. The piston 7 also carries thermal insulation 12 adjacent to its end face 9. The cylindrical housing 6 is made double-walled and has pockets 13 which are connected to a circuit of a cooling medium, water at 15° C., for example. The flow passes through the cylindrical housing 6 in the direction of the arrows 14, 15. This water circuit or the cooling of the cylindrical housing 6 and finally of the measuring chamber 8 caused by it brings the liquid chocolate mass to solidification under reproducible conditions.

Figure 2:
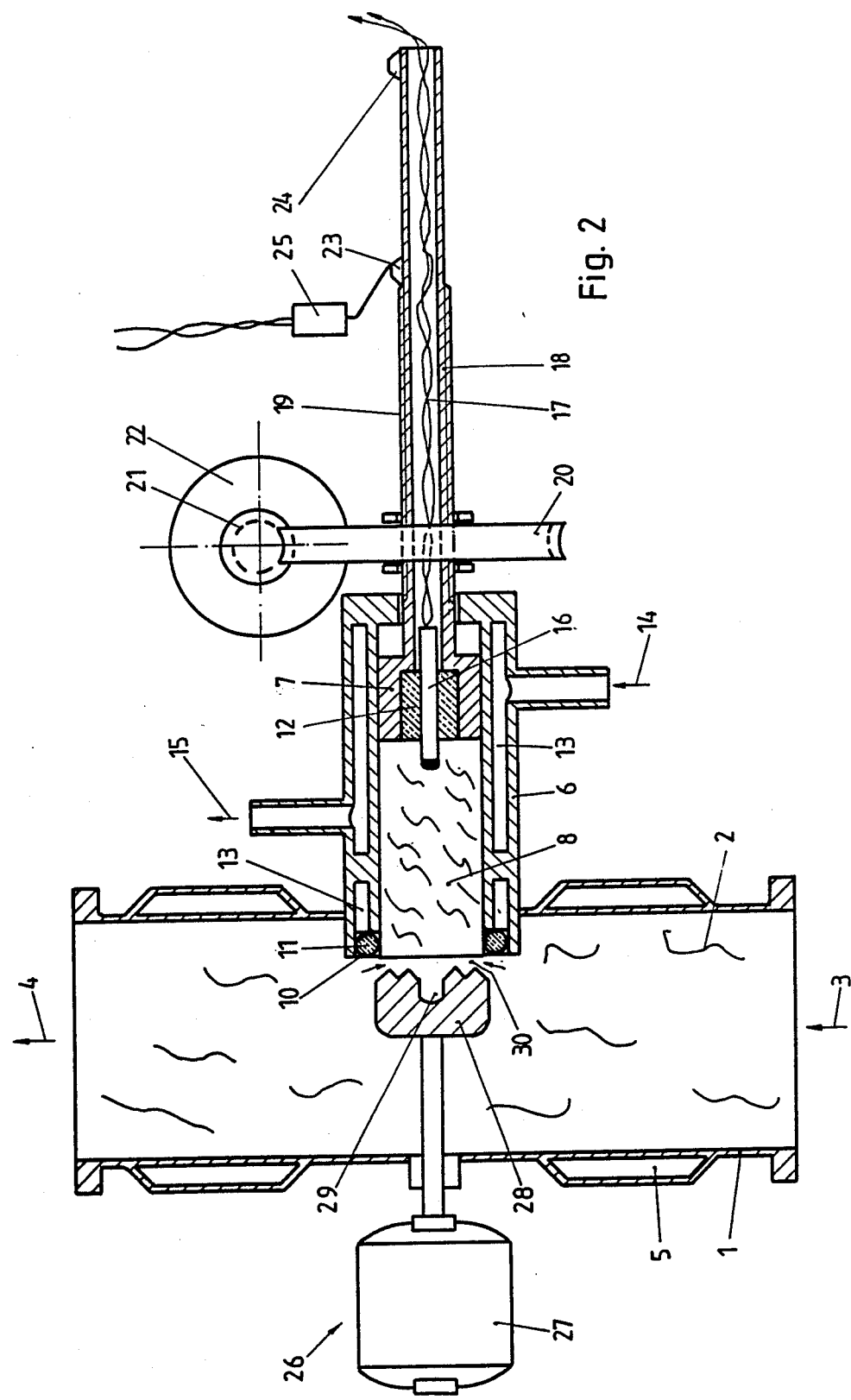
FIG. 2 shows the apparatus towards the end of the suction stroke and FIG. 3 shows the apparatus during the ejection and removal of a slug of solidified chocolate mass.
Figure 3:
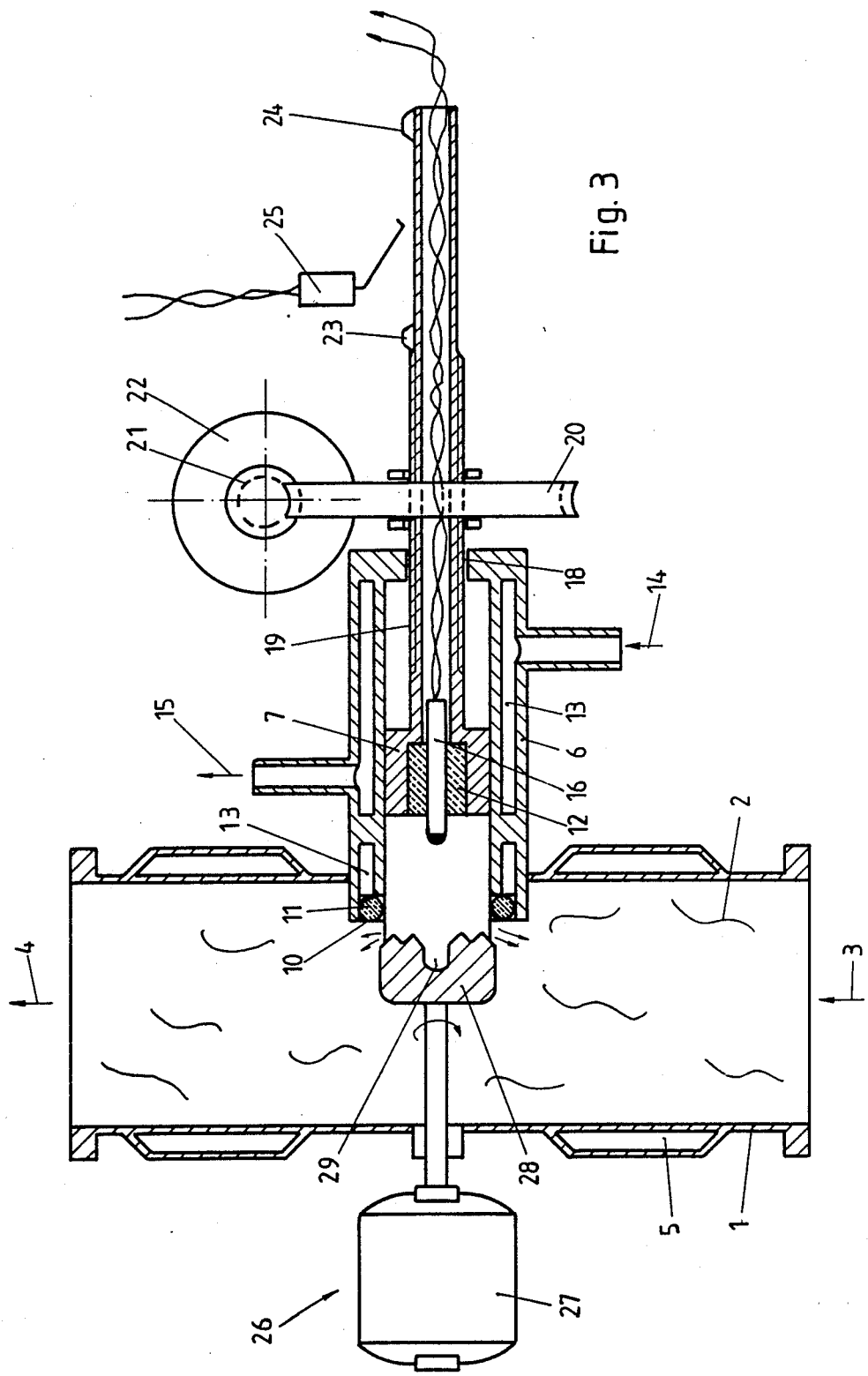

Mounted fixedly in place in the piston 7 coaxially or centrally and so as to project beyond the end face 9 is a temperature-measuring sensor 16 which can be designed as a thermalcouple, a semiconductor sensor, a resistance element or the like. Electrical leads 17 are guided outwards through a hollow extension 18 of the piston 7. These can be designed as a threaded spindle 19 on its outside, and serve to transmit the particular readings of the temperature-measuring sensor 16 to a device for recording the temperature pattern, which is not shown for the sake of clarity. Such a device can consist of a pen-type recording instrument, a control unit for a heat-treatment machine or the like. A worm wheel 20 is arranged on the threaded spindle 19 but is guided so as to be axially non-displaceable. The worm wheel 20 interacts with a worm 21 which is driven by a motor 22. As a result of the rotation of the worm wheel 20 which is guided so as to be axially non-displaceable, in conjunction with the threaded spindle 19. The rotation is converted into a translational movement, which is the stroke of the piston 7, so that the latter can execute a to-and-fro stroke according to the two directions of rotation of the motor 22. In particular, a suction stroke as a comparison between FIGS. 1 and 2 is shown, along with an ejection stroke, as can be seen from FIG. 3. Of course, the reversing stroke of the piston 7 can also be carried out in another way and a drive can be designed for this. It is only essential that the piston 7 can be moved to and fro in a controlled manner, so that during the suction stroke, the measuring chamber 8 can fill with the liquid chocolate mass and, during the ejection stroke, the solidified chocolate slug is ejected from the measuring chamber 8. The stroke of the piston can be fixed by means of two cams 23 and 24, which are located on the threaded spindle 19 and which can also be made lockable and therefore adjustable. A limit switch 25 cooperates with the two cams 23 and 24, as can be seen from the interplay shown in FIGS. 1 to 3.

A device 26 for removing the solidified sample from the piston 7 and temperature-measuring sensor 16 is arranged axially in line with the measuring chamber, but nevertheless opposite this. This device 26 is designed as a mechanical comminuting device and, for example, has a motor 27 and a milling head 28. This milling head 28 is mounted fixed in place, but rotatably, so that when the solidified chocolate slug is pushed out (FIG. 3), the milling head 28 mills it into very small pieces which are absorbed by the stream of liquid chocolate mass 2 and thus returned to the circuit. The fear that solid chocolate pieces carried along will cause damage in a further-processing machine is hereby eliminated. As the Figures show, the milling head, in its center, has a recess 29 which is matched to the projecting length of the temperature-measuring sensor 16 from the end face 9 of the piston 7 so that, in the end, the region around the measuring sensor 16 is also cleaned.

Instead of such a milling device 26, a stationary cutting-knife combination could also be arranged in front of and on the cylindrical housing 6 or its end face 9. This would ensure that the solidified chocolate slug from the measuring chamber 8 is comminuted mechanically during ejection. Of course, a proportionately better effect is achieved by means of a driven mechanical device 26. It is also possible to mount or guide the device 26, so that it is axially displaceable, in order thereby to obtain interaction with the piston 7 of the piston/cylinder unit 6/7. This is necessary especially when the front dead center of the piston 7 is arranged so that it does not project beyond the end face 10 with its end face 9. However, if the conditions are reversed, as shown in the drawing, then the device 26 can be arranged so as to be axially non-displaceable; that is, to be fixed in place. Nevertheless, a sufficiently large annular gap 30, through which the liquid chocolate mass can flow into the measuring chamber 8 unimpeded by the milling head 28, forms at the start of the suction stroke of the piston 7.

The apparatus works as follows: The suction stroke is initiated from the state of rest according to FIG. 1, by driving the motor 22 in such a direction of rotation that the piston 7 moves backwards in the cylindrical housing 6, as shown by comparison of FIGS. 1 and 2. The liquid chocolate mass 2 thereby flows into the measuring chamber 8 via the annular gap 30. This inflow action ends when the piston 7 reaches its rear dead-center position according to FIG. 2. In the rear dead-center position, the measuring sensor 16 always has the same relative position in relation to the liquid chocolate mass in the measuring chamber 8, so that its temperature pattern can be measured in a reproducible way over a period of time. The cooling circuit appropriately flows continuously through the double-walled cylindrical housing 6 or the pockets 13, so that a corresponding elimination of heat takes place via this wall, and the liquid chocolate mass solidifies progressively in the measuring chamber 8. When this temperature pattern has been recorded, by means of a pen-type recording instrument, for example, and the temperature creeps outside the measuring range, this can be a signal to start the ejecting stroke of the piston 7. For this purpose, the motor 22 is driven oppositely to the direction of rotation during the suction stroke, so that the piston 7 ejects the solidified slug of chocolate mass according to FIG. 3. Simultaneously, with this ejection movement, the motor 27 of the device 26 is set in motion, so that the milling head 28 mills the chocolate mass of the slug into very small pieces which are absorbed by the liquid chocolate mass 2 flowing past and which are subsequently melted. The piston 7 then moves into its front dead-center position according to FIG. 1 again, whereupon the apparatus assumes the state of rest, until a new measurement takes place. This can be initiated or controlled by means of a program as a function of time or of other control operations.

List of reference symbols

1 Pipeline section
2 Chocolate mass
3 Arrow
4 Arrow
5 Pocket
6 Cylindrical housing
7 Piston
8 Measuring chamber
9 End face
10 End face
11 Thermal insulation
12 Thermal insulation
13 Pockets
14 Arrow
15 Arrow
16 Temperature-measuring sensor
17 Electrical leads
18 Extension
19 Threaded spindle
20 Worm wheel
21 Worm
22 Motor
23 Cam
24 Cam
25 Limit switch
26 Device
27 Motor
28 Milling head
29 Recess
30 Annular gap

I claim:

1. Apparatus for determining crystallization solidification curves of chocolate masses and similar fatty masses, comprising: measuring means with a chamber formed by a cooled wall; a temperature-measuring sensor projecting into said chamber, liquid chocolate mass being brought to solidification in said chamber, said chocolate mass having a temperature pattern while solidifying; means for recording said temperature pattern as a function of time; piston means and cylinder means in said chamber, said piston means having an end face; said cylinder means having an open end face extending into said chocolate mass; drive means for reciprocating said piston; and mechanical comminuting means for removing a solidified sample of said chocolate mass from said piston and said sensor.

2. Apparatus as defined in claim 1, wherein said cylinder means has said open end face, said piston bordering said chamber and being extendible into said chocolate mass up to a point beyond said open end face of said cylinder means.

3. Apparatus as defined in claim 1, wherein said mechanical comminuting means comprises milling means.

4. Apparatus as defined in claim 1, wherein said mechanical comminuting means comprises cutting means.

5. Apparatus as defined in claim 1, wherein said piston has an end face, said mechanical comminuting means being arranged opposite said chamber and adjacent to said end face of said piston when said piston is in extended position.

6. Apparatus as defined in claim 1, including a cooling circuit of constant temperature; said piston and cylinder means having a double wall connected to said cooling circuit.

7. Apparatus as defined in claim 1, wherein said drive means for reciprocating said piston comprises reversible means with an adjustable stroke.

8. Apparatus as defined in claim 1, wherein said drive means comprises a spindle motor with a step-down gear; said piston having a threaded spindle and a rear side, said threaded spindle being on said rear side of said piston.

9. Apparatus as defined in claim 1, wherein said cylinder means has thermal insulation in a region of said open end face.

10. Apparatus as defined in claim 1, including thermal insulation means in a region of said end face of said piston.

11. Apparatus for determining crystallization solidification curves of chocolate masses and similar fatty masses, comprising: measuring means with a chamber formed by a cooled wall; a temperature-measuring sensor projecting into said chamber, liquid chocolate mass being brought to solidification in said chamber, said chocolate mass having a temperature pattern while solidifying; means for recording said temperature pattern as a function of time; piston means and cylinder means in said chamber, said piston means having an end face; said cylinder means having an open end face extending into said chocolate mass; drive means for reciprocating said piston; and mechanical comminuting means for removing a solidified sample of said chocolate mass from said piston and said sensor; said piston having an end face, said temperature-measuring sensor being arranged centrally on said piston for projecting beyond said end face of said piston.

* * * * *